US008157724B2

(12) United States Patent
Lee

(10) Patent No.: US 8,157,724 B2
(45) Date of Patent: Apr. 17, 2012

(54) FEMALE RELAXATION DEVICE

(76) Inventor: Yiu Kwong Lee, Hong Kong (HK)

( * ) Notice: Subject to any disclaimer, the term of this patent is extended or adjusted under 35 U.S.C. 154(b) by 918 days.

(21) Appl. No.: 12/279,064

(22) PCT Filed: May 11, 2007

(86) PCT No.: PCT/CN2007/001535
§ 371 (c)(1),
(2), (4) Date: Aug. 12, 2008

(87) PCT Pub. No.: WO2007/131440
PCT Pub. Date: Nov. 22, 2007

(65) Prior Publication Data
US 2009/0036732 A1 Feb. 5, 2009

(30) Foreign Application Priority Data
May 17, 2006 (CN) .......................... 2006 1 0035554

(51) Int. Cl.
*A61F 5/00* (2006.01)

(52) U.S. Cl. ......................................................... 600/38

(58) Field of Classification Search ............. 600/38–41; 601/46, 55
See application file for complete search history.

(56) References Cited

U.S. PATENT DOCUMENTS

| | | | | |
|---|---|---|---|---|
| 3,598,106 | A * | 8/1971 | Buning | 600/591 |
| 5,920,923 | A * | 7/1999 | Jillette | 4/541.1 |
| 2005/0234292 | A1* | 10/2005 | Faulkner et al. | 600/38 |
| 2006/0041210 | A1* | 2/2006 | Regey | 601/148 |

* cited by examiner

*Primary Examiner* — John Lacyk

(57) ABSTRACT

A female relaxation device comprises an inserting portion. The inserting portion includes a clubbed heat-conducting body (11), and a water flow channel disposed in the heat-conducting body (11). The water flow channel includes an inlet (12) and an outlet (13), both of which are disposed in one end of the heat-conducting body (11). The female relaxation device also includes a water providing apparatus for providing the water flow of determined temperature to the water flow channel through connecting with the inlet (12) and the outlet (13). A female is stimulated to reach a climax by providing water flow of the determined temperature to the heat-conducting body from the water providing apparatus and adjusting the water temperature.

12 Claims, 2 Drawing Sheets

FEMALE RELAXATION DEVICE

BACKGROUND OF THE INVENTION

1. Field of the Invention

The present invention relates to female sexual health article, special to female relaxation device.

2. Description of Prior Art

In the busy living, the sexual requirement of the females is ignored by the males in middle age. Much more, the modern females being independent, the feelings of emptiness and aloneness are formed in the life of the mid-age females as to make the females' emotion bad and worried. Besides, due to the lack of sexual life, the secretion of the female hormone is effected to make the sexual frigidity and the like ascend. Now some female self-consolations appear in the market to solve the problem of the females' sexual requirement, which generally comprises a rod-like inserting portion that is controlled manually to fillip the sexual organ of the females for the sexual orgasm to satisfy the sexual requirement of the females. Advantageously, vibrational motors are mounted in the inserting portion of the self-consolation to increase stimulation for satisfying the sexual requirement of the females. Since the temperature of the self-consolation cannot be adjusted, it is not comfortable to the females when it is used in the cold weather. Furthermore, it is controlled manually; thereby it can not satisfy the females' sexual requirement.

SUMMARY

Accordingly, an object of the present invention is to provide a female relaxation device to stimulate to reach a climax of female by providing water flow of determined temperature.

An object of the present invention is to provide a female relaxation device comprising an inserting portion, wherein the inserting portion comprises a clubbed heat-conducting body and a water flow channel disposed in the heat-conducting body; the water flow channel comprises a inlet and a outlet disposed in one end of the heat-conducting body; the female relaxation device further comprises a water providing apparatus which is communicated with the inlet and the outlet to provide water flow into the water flow channel in determined temperature.

Advantageously, the clubbed heat-conducting body is a metal stick or a heat conduction stick of silica gel with a hollow chamber; the water flow channel comprises an influent pipe disposed in the hollow metal stick; one end of the influent pipe is the inlet, and the other end of the influent pipe is communicated with the hollow chamber; the outlet is disposed in the end of the hollow chamber.

Advantageously, the water providing apparatus comprises a controller, an inductor, a heater, a storage tank communicated with the inlet and the outlet and a water supply pump; the heater is controlled by the controller according to the water temperature detected by the inductor, and the water supply pump is controlled by the controller to introduce the water flow into the water flow channel.

Advantageously, the heat-conducting body is pestle-shaped, and the size of one end nearby the inlet and the outlet is smaller than the size of the other end which is apart from the end nearby the inlet and the outlet.

Advantageously, an anti-thrust colloid portion is disposed in the position on the heat-conducting body which is near the inlet and the outlet.

Advantageously, a driving reciprocator driving the inserting portion to move back and forth alternately is connected with one end of the heat-conducting body nearby the inlet and the outlet.

Advantageously, the driving reciprocator comprises a base, an adjustable speed motor mounted on the base, a push rod connected with the heat-conducting body by a ball ream, a brace structure connected with the protrudent axis of the adjustable speed motor to make the push rod to moving back and forth alternately, and a guide structure allowing the push rod to move in the determined direction.

Advantageously, the brace structure comprises a librating rod of one end fixing with the protrudent axis of the adjustable speed motor, and a connecting rod of one end being connected to the other end of the librating rod rotationally; the other end of the connecting rod is connected to the push rod rotationally by pin.

Advantageously, the guide structure comprises pulley block fixed on the base in parallel and guide groove disposed in the push rod to match the pulley block; or the guide structure is a sleeve disposed on the push rod.

Advantageously, the heat-conducting body is a two-partwise structure.

According to the present invention, a water flow of determined temperature is provided for the water flow channel of the heat-conducting body by the water providing apparatus, so that the females' sexual organ can be stimulated to reach a climax by the cold-warm impact of the temperature of the water flow. It has a good stimulative effect to assist the female to reach a climax for a good sexual life, thereby reducing the pressure of the females' living. It also allows the hormone to secrete normally to decrease the females' hidden illness. Furthermore, it allows the heat-conducting body to be driven to move back and forth alternately by the driving reciprocator without manual control, which attains more convenience when using.

DETAILED DESCRIPTION

As shown from FIG. 1 to FIG. 4, a female relaxation device according to the present invention comprises an inserting portion and a driving reciprocator which drives the inserting portion moving back and forth alternately. It can be understood that the driving reciprocator can also be replaced by manually controlling the inserting portion.

Figure 1:
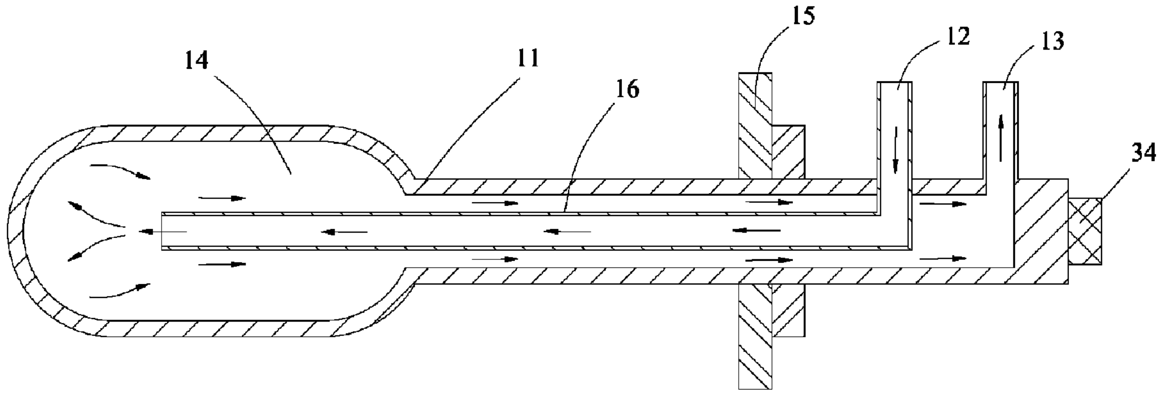
FIG. 1 shows a sectional view of an embodiment of the inserting portion of the female relaxation device according to the present invention.

The inserting portion comprises a clubbed heat-conducting body 11 and a water flow channel which is disposed in the heat-conducting body 11. As shown in FIG. 1, in the present embodiment, the water flow channel comprises an inlet 12 and an outlet which are disposed in one end of the heat-conducting body 11. The female relaxation device also comprises a water providing apparatus (not shown in FIG. 1) which provides water flow of determined temperature to the water flow channel through connecting with the inlet 12 and the outlet 13. The determined temperature of the water flow can be adjusted according to the work time, inserted depth of the inserting portion and so on, so as to achieve continuous cool and warm feeling stimulated female to reach a climax.

Figure 2:
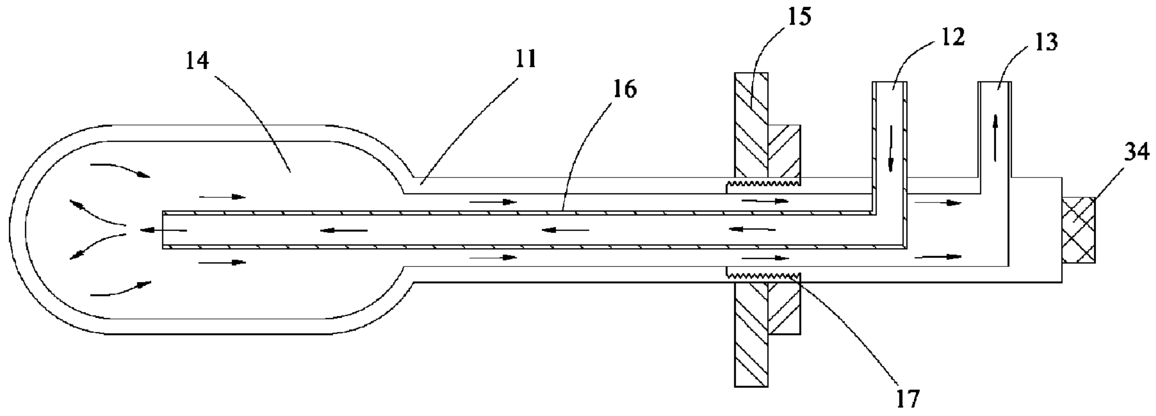
FIG. 2 shows a sectional view of the detachable inserting portion of the female relaxation device according to the present invention.

The clubbed heat-conducting body 11 is metal stick with a hollow chamber 14. In the present embodiment, the heat-conducting body 11 is pestle-shaped, and the size of one end nearby the inlet 12 and the outlet 13 is smaller than the size of other end which is apart from the end nearby the inlet 12 and the outlet 13, thereby producing lager friction when the heat-conducting body 11 steps into and drop out from the females' sexual organ. The heat-conducting body can also use hollow heat conduction stick of silica gel to replace the metal stick. An anti-thrust colloid portion 15 is disposed in the position on the heat-conducting body 11 which is near the inlet 12 and the outlet 13, thereby preventing the heat-conducting body 11 from stepping into the females' sexual organ too deeply causing undesired injury. As shown in FIG. 2, the heat-conducting body 11 can also be designed to be a separate two-part-wise structure. In FIG. 2, the heat-conducting body 11 is partitioned into two parts at the position of the anti-thrust colloid portion 15, which are connected by a thread 17 (other detachable buckle structure connections can also be utilized here) to detach the two parts for cleaning after being used.

As shown in FIG. 1, in the present embodiment, the water flow channel comprises an influent pipe 16 disposed in the hollow metal stick and a hollow chamber 14 in the metal stick. One end of the influent pipe 16 is the inlet 12, and the other end is stepped into the hollow chamber 14 and communicated with the hollow chamber 14. The outlet 13 is disposed in the end of the hollow chamber 14 and the direction of the water flow is shown as the arrow in the drawing. As shown in the FIG. the influent pipe 16 is configured to insert into the intermediate position of the hollow chamber 14, Of course it can also be inserted into the position apart from the intermediate position.

Another embodiment of the water flow channel is shown in FIG. 2, the water flow channel is formed by a crooked pipe 26. The pipe 26 can be made to match the shape of the hollow chamber 14 defined in the heat-conducting body 11 for conducting heat sufficiently. The pipe 26 is attached to the inner wall of the hollow chamber 14 of the heat-conducting body 11. The water flow from a water providing apparatus flows in the pipe 26, as the direction of the arrow shown in the Fig., and the heat is transferred to the heat-conducting body 11. The adjustment of the temperature of the heat-conducting body 11 is implemented to fillip the female by the cold-warm feeling.

The water flow in determined temperature for the water flow channel is provided by the water providing apparatus. The water providing apparatus connect with flowing water-head, and allows the water flow to be heated using a heating device and allows the water flow to be introduced to the water flow channel. In the present embodiment, the water providing apparatus comprises a controller, an inductor, a heater, a storage tank and a water supply pump. A determined quantity of water is stored in the storage tank, which is communicated with the inlet 12 and the outlet 13 to introduce the water flow from the inlet 12 to the water flow channel and recycle the water flow from the outlet 13 for recycling use. The inductor is configured to detect the water temperature of the storage tank and transfer the output signal to the controller. Then the heater is controlled by the controller according to the water temperature which is detected by the inductor. The water in the storage tank is heated by the heater and the water supply pump is controlled by the controller to introduce the water flow to the water flow channel.

Figure 3:
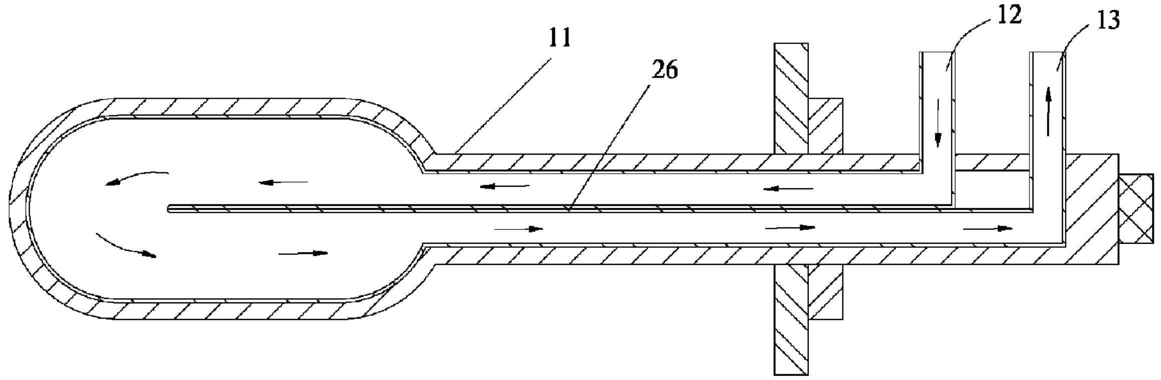
FIG. 3 shows a sectional view of another embodiment of the inserting portion of the female relaxation device according to the present invention.
Figure 4:
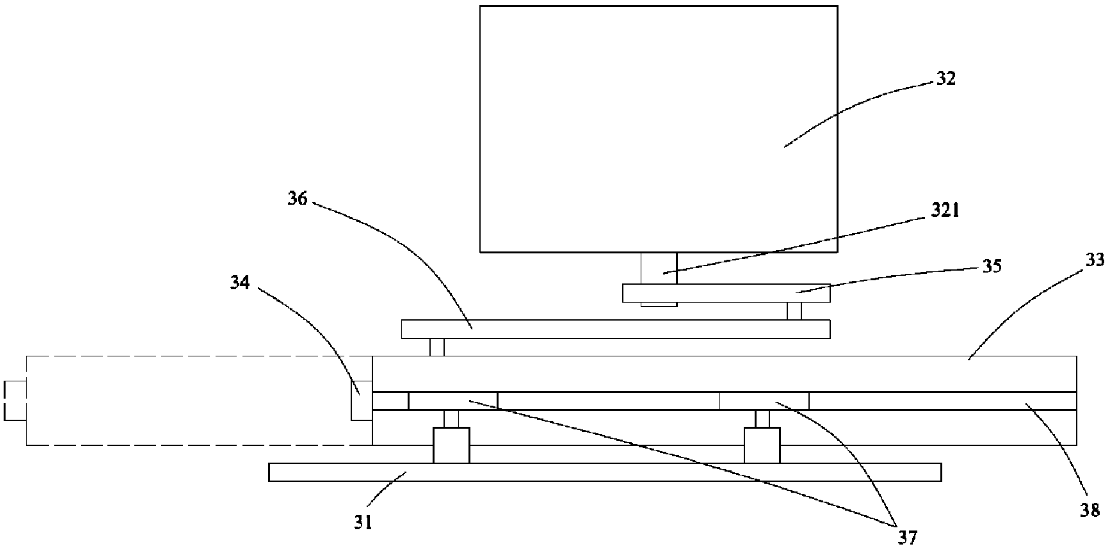
FIG. 4 shows the driving reciprocator of the female relaxation device according to the present invention.
Figure 5:
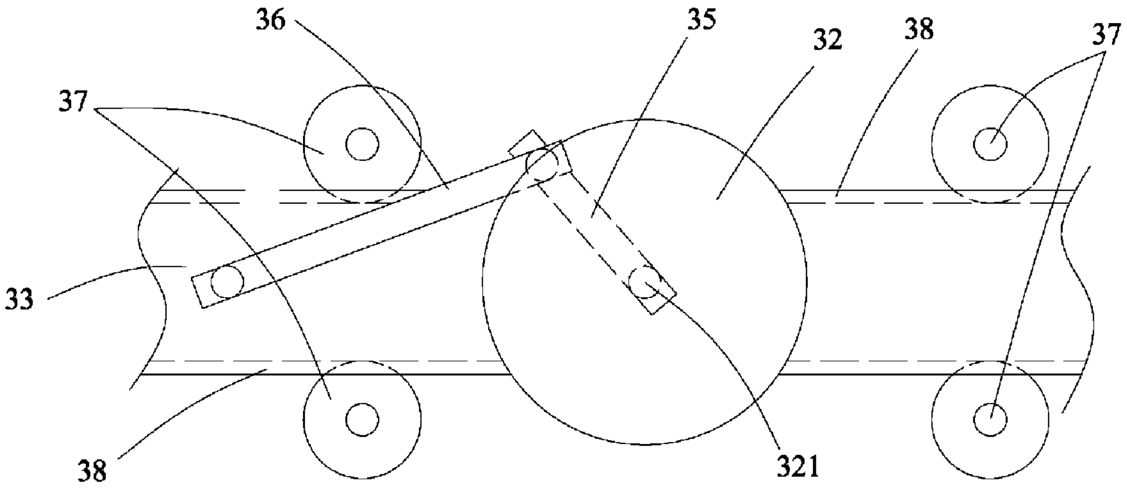
FIG. 5 shows another part view of the driving reciprocator of the female relaxation device according to the present invention.
Figure 6:
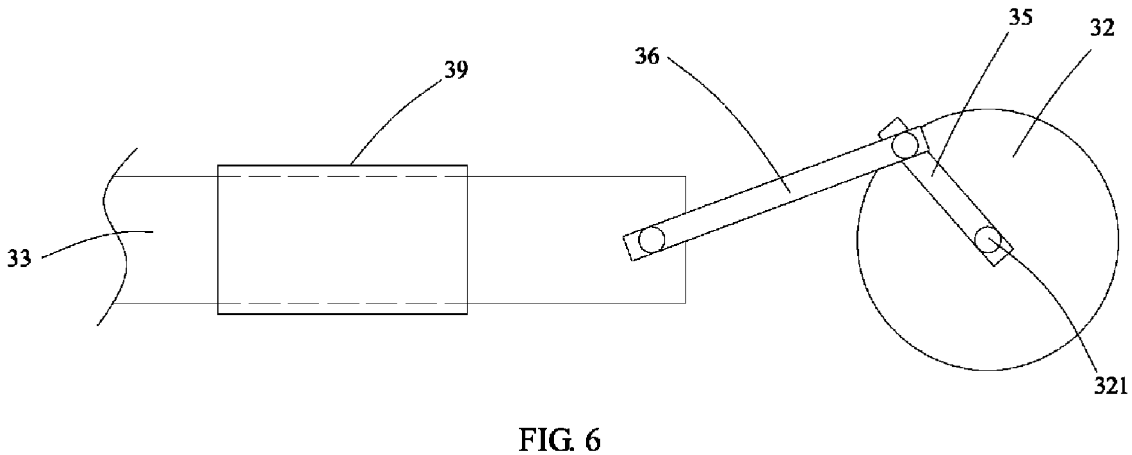
FIG. 6 shows a part sectional view of another embodiment of the guide structure of the driving reciprocator of the female relaxation device according to the present invention.

The driving reciprocator is disposed in one end of the heat condition body 11 which is near the inlet 12 and the outlet 13. As shown in FIG. 3 and FIG. 4, in the present embodiment, the driving reciprocator comprises a base 31, an adjustable speed motor 32 mounted on the base 31, a push rod 33 connected with the heat-conducting body 11 by a ball ream 34, a brace structure connected with the protrudent axis 321 of the adjustable speed motor 32 to make the push rod 33 moving back and forth alternately, and a guide structure allowing the push rod 33 to move in the determined direction. The brace structure comprises librating rod 35 of one end fixing with the proturdent axis 321 of the adjustable speed motor 32, and connecting rod 36 of one end being connected with the other end of the librating rod 35 rotationally. The other end of the connecting rod 36 is connected to the push rod 33 rotationally by pin. Of course, the brace structure can be replaced with eccenter structure. The guide structure comprises pulley block 37 fixed on the base 31 in parallel and guide groove 38 disposed in the push rod 33 to match the pulley block 37. As shown in FIG. 6, the guide structure according to the present invention can be disposed in the periphery of the push rod 33 by using a sleeve 39 to define the moving direction of the push rod 33. Certainly, the guide structure can be implemented by a runner and a matchable path.

According to the motion, the protrudent axis 321 of the motor 32 rotates to drive the librating rod 35 to rotate. The librating rod 35 drives the connecting rod 36 to rotate, and the connecting rod 36 drives the push rod 33 to move. The push rod 33 cannot rotate in the limitation of the guide structure, but it can reciprocate in the determined direction defined by the guide structure (as shown in the dashed position). Therefore it allows the inserting portion to move back and forth alternately without manual control, which attains more convenience when using.

I claim:

1. A female relaxation device comprising an inserting portion, wherein the inserting portion comprises a clubbed heat-conducting body and a water flow channel disposed in the heat-conducting body;

the water flow channel comprises an inlet and an outlet disposed in one end of the heat-conducting body;

the female relaxation device further comprises a water providing apparatus which is communicated with the inlet and the outlet to provide water flow into the water flow channel in determined temperature.

2. The female relaxation device as described in claim 1, wherein the clubbed heat-conducting body is a metal stick or a heat conduction stick of silica gel with a hollow chamber; the water flow channel comprises an influent pipe disposed in the hollow metal stick; one end of the influent pipe is the inlet, and the other end of the influent pipe is communicated with the hollow chamber; the outlet is disposed in the end of the hollow chamber.

3. The female relaxation device as described in claim 1, wherein the water providing apparatus comprises a controller, an inductor, a heater, a storage tank communicated with the inlet and the outlet and a water supply pump;

the heater is controlled by the controller according to the water temperature detected by the inductor, and the water supply pump is controlled by the controller to introduce the water flow into the water flow channel.

4. The female relaxation device as described in claim 3, wherein the heat-conducting body is pestle-shaped, and the size of one end nearby the inlet and the outlet is smaller than the size of the other end which is apart from the end nearby the inlet and the outlet.

5. The female relaxation device as described in claim 4, wherein an anti-thrust colloid portion is disposed in the position on the heat-conducting body which is near the inlet and the outlet.

6. The female relaxation device as described in claim 4, wherein a driving reciprocator driving the inserting portion to move back and forth alternately is connected with one end of the heat-conducting body nearby the inlet and the outlet.

7. The female relaxation device as described in claim 6, wherein the driving reciprocator comprises a base, an adjustable speed motor mounted on the base, a push rod connected with the heat-conducting body by a ball ream, a brace structure connected with the protrudent axis of the adjustable speed motor to make the push rod moving back and forth alternately, and a guide structure allowing the push rod to move in the determined direction.

8. The female relaxation device as described in claim 7, wherein the brace structure comprises a librating rod of one end fixing with the protrudent axis of the adjustable speed motor, and a connecting rod of one end being connected to the other end of the librating rod rotationally; the other end of the connecting rod is connected to the push rod rotationally by pin.

9. The female relaxation device as described in claim 8, wherein the guide structure comprises pulley block fixed on the base in parallel and guide groove disposed in the push rod to match the pulley block.

10. The female relaxation device as described in claim 2, wherein the heat-conducting body is a two-part-wise structure.

11. The female relaxation device as described in claim 2, wherein the water providing apparatus comprises a controller, an inductor, a heater, a storage tank communicated with the inlet and the outlet and a water supply pump;

the heater is controlled by the controller according to the water temperature detected by the inductor, and the water supply pump is controlled by the controller to introduce the water flow into the water flow channel.

12. The female relaxation device as described in claim 8, wherein the guide structure is a sleeve disposed on the push rod.

* * * * *